(12) United States Patent
Middlebrook et al.

(10) Patent No.: US 10,173,220 B2
(45) Date of Patent: Jan. 8, 2019

(54) DEVICES AND METHODS FOR DISSOCIATING A BIOLOGICAL TISSUE SAMPLE

(71) Applicant: Becton, Dickinson and Company, Franklin Lakes, NJ (US)

(72) Inventors: Aaron J. Middlebrook, San Jose, CA (US); Smita Ghanekar, Fremont, CA (US); Brian David Warner, Martinez, CA (US); Albert Mach, San Jose, CA (US); David Vrane, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 617 days.

(21) Appl. No.: 14/817,789

(22) Filed: Aug. 4, 2015

(65) Prior Publication Data

US 2016/0069781 A1    Mar. 10, 2016

Related U.S. Application Data

(60) Provisional application No. 62/046,047, filed on Sep. 4, 2014.

(51) Int. Cl.
*G01N 1/28* (2006.01)
*B02C 1/14* (2006.01)
*B02C 18/02* (2006.01)
*B02C 19/08* (2006.01)
*C12M 1/33* (2006.01)

(52) U.S. Cl.
CPC ............... *B02C 1/14* (2013.01); *B02C 18/02* (2013.01); *B02C 19/08* (2013.01); *C12M 45/02* (2013.01); *G01N 1/286* (2013.01); *G01N 2001/2866* (2013.01)

(58) Field of Classification Search
CPC ........... G01N 1/286; G01N 2001/2866; C12M 45/02; B02C 1/14; B02C 18/02; B02C 19/08
See application file for complete search history.

(56) References Cited

U.S. PATENT DOCUMENTS

| 3,028,314 A | 4/1962 | Means et al. |
| 3,666,187 A | 5/1972 | Norris |
| 3,938,784 A | 2/1976 | Moreton |
| 4,828,395 A | 5/1989 | Saito et al. |

(Continued)

FOREIGN PATENT DOCUMENTS

KR    10-2013-0045465 A    5/2013

OTHER PUBLICATIONS

Burden, David W. "Guide to the Homogenization of Biological Samples", Random Primers, Issue No. 7, Sep. 2008, pp. 1-14.

(Continued)

*Primary Examiner* — Omar Flores Sanchez
(74) *Attorney, Agent, or Firm* — Bret E. Field; Bozicevic, Field & Francis LLP

(57) ABSTRACT

Tissue dissociators configured to disrupt a biological tissue sample are provided. Aspects of the tissue dissociators may include a housing having a distal end and a proximal end, a cutting blade positioned at the distal end of the housing and a tissue actuator configured to be displaced along a longitudinal axis within the housing. Also provided are methods of using the tissue dissociators, as well as kits including the tissue dissociators.

20 Claims, 12 Drawing Sheets

(56) References Cited

U.S. PATENT DOCUMENTS

| | | | |
|---|---|---|---|
| 5,035,708 A | 7/1991 | Alchas et al. | |
| 5,330,914 A | 7/1994 | Uhlen et al. | |
| 5,372,945 A | 12/1994 | Alchas et al. | |
| 5,409,833 A | 4/1995 | Hu et al. | |
| 5,610,074 A | 3/1997 | Beritashvili et al. | |
| 5,731,199 A | 3/1998 | Roggero | |
| 5,786,207 A | 7/1998 | Katz et al. | |
| 2002/0197631 A1* | 12/2002 | Lawrence | B01L 3/502 435/270 |
| 2004/0018575 A1* | 1/2004 | Rappin | B01L 3/502 435/7.92 |
| 2004/0043701 A1 | 3/2004 | Garland | |
| 2004/0146434 A1* | 7/2004 | Kane | B01F 3/18 422/534 |
| 2005/0139704 A1 | 6/2005 | Liao et al. | |
| 2007/0082389 A1* | 4/2007 | Clark | C12M 45/02 435/287.2 |
| 2007/0148756 A1 | 6/2007 | Bullen et al. | |
| 2007/0166834 A1* | 7/2007 | Williamson, IV | G01N 1/286 436/174 |
| 2009/0084202 A1* | 4/2009 | Mimori | G01N 1/286 73/864.91 |
| 2012/0201726 A1 | 8/2012 | Pearcy et al. | |
| 2013/0028813 A1 | 1/2013 | Shioyama et al. | |

OTHER PUBLICATIONS

Cunningham, Robert E. "Chapter 27: Tissue Disaggregation", Immunocytochemical Methods and Protocols, Methods in Molecular Biology, vol. 34, 1994, pp. 225-228.

Cunningham, Robert E. "Chapter 32: Tissue Disaggregation", Immunocytochemical Methods and Protocols Methods in Molecular Biology, vol. 588, 2010, pp. 327-330.

Invitrogen Corporation, "Tissue Homogenization Procedures for use with ELISA", Product Sheet, 2008, pp. 1-8.

Smeets et al. "Comparison of Tissue Disaggregation Techniques of Transitional Cell Bladder Carcinomas for Flow Cytometry and Chromosomal Analysis", Cytometry 8, 1987, pp. 14-19.

Notification of the First Office Action for Chinese patent application serial No. 201580045929.9, dated Jul. 27, 2018, 4 pages.

* cited by examiner

DEVICES AND METHODS FOR DISSOCIATING A BIOLOGICAL TISSUE SAMPLE

CROSS-REFERENCE TO RELATED APPLICATIONS

This application claims priority to U.S. Provisional Patent Application Ser. No. 62/046,047, filed on Sep. 4, 2014, the disclosure of which is incorporated herein by reference.

INTRODUCTION

Processing a biological tissue sample is often necessary in numerous therapeutic, diagnostic and research applications. Tissue processing to achieve desired single cell compositions is commonly accomplished by mechanical disruption followed by enzymatic digestion. In general, the efficiency and effectiveness of enzymatic digestion is proportional to the surface area of the tissue-enzyme interface. Increased surface area can be achieved by mincing the tissue by mechanical means prior to enzymatic exposure. Tissue dissociation can often require laborious separation protocols and numerous manipulations of the tissue in order to separate the desired tissue sample from other biological material. Over-processing of the tissue can sometimes lead to significant increases in cell death i.e., loss of functional viability and/or morphological damage, and under-processing, often achieved through manual cutting using scalpel blades in a petri dish, results in tissue pieces that can have a wide range of size distribution varying enormously from one sample to the next or one operator to the next. Likewise, time required to process certain sample types (e.g., healthy tissues) may require a different extent of dissociation than others (e.g., cancerous or necrotic tissue), making dissociation of complex biological samples difficult and inefficient.

There is a constant need for the development of simplified tissue sample preparation methods which deliver high quality and enriched tissue samples for use in a variety of different therapeutic, diagnostic and research applications. Devices and methods that provide high quality tissue samples with little to no loss (physical or functional) are of interest.

SUMMARY

Aspects of the present disclosure include tissue dissociators configured to disrupt a biological tissue sample. Tissue dissociators according to certain embodiments include a housing having a distal end and a proximal end, a cutting blade positioned at the distal end of the housing and a tissue actuator configured to be displaced along a longitudinal axis within the housing. Tissue actuators, in some embodiments, include a fluid reservoir which extends from a proximal end to a distal end of the tissue actuator and a plunger configured to be displaced along a longitudinal axis within the fluid reservoir.

Aspects of the disclosure also include methods for dissociating a biological tissue sample. Methods according to certain embodiments include inserting a biological tissue into a tissue dissociator housing, pressing the biological tissue against cutting blades positioned at the distal end of the housing by displacing the tissue actuator from the proximal end to the distal end of the housing in a manner sufficient to produce a dissociated biological tissue sample having components of identical shape and size. Kits which include a housing, a cutting blade and a tissue actuator configured to be displaced along a longitudinal axis within the housing are also provided.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1A:
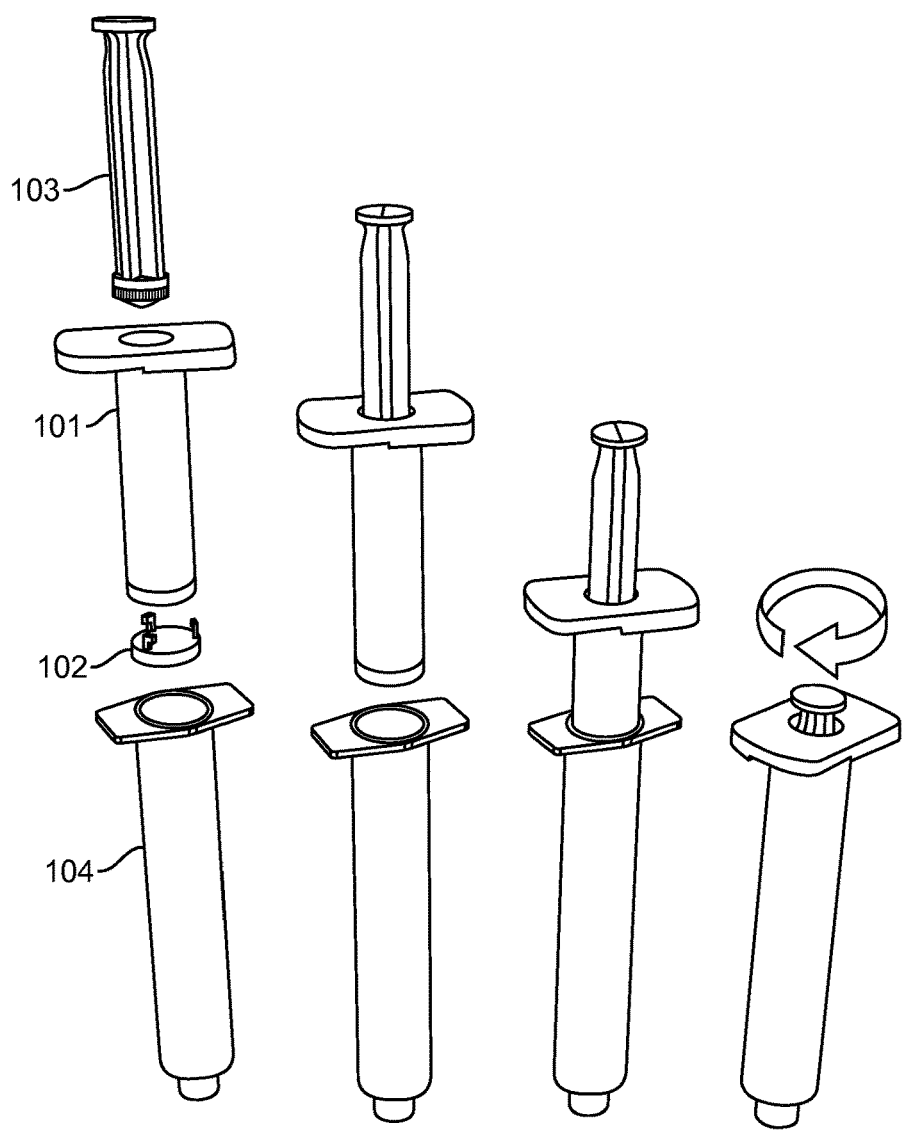
FIG. 1A depicts the configuration of a tissue dissociator inside a container according to certain embodiments.

Tissue dissociators configured to disrupt a biological tissue sample are provided. Aspects of the tissue dissociators may include a housing having a distal end and a proximal end, a cutting blade positioned at the distal end of the housing and a tissue actuator configured to be displaced along a longitudinal axis within the housing. Also provided are methods of using the tissue dissociators, as well as kits including the tissue dissociators.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides a tissue dissociator configured to disrupt a biological tissue sample. In further describing embodiments of the disclosure, tissue dissociators that include a housing having a distal end and a proximal end, a cutting blade positioned at the distal end of the housing and a tissue actuator configured to be displaced along a longitudinal axis within the housing are first described in greater detail. Next, methods for preparing a dissociated biological tissue sample with the subject tissue dissociators are described. Kits for preparing a dissociated biological tissue sample are also provided.

Devices for Dissociating a Biological Tissue Sample

As summarized above, aspects of the present disclosure include a tissue dissociator configured to dissociate a biological tissue sample. The term "dissociate" is used herein in its conventional sense to refer to breaking up and separating the biological tissue sample into a plurality of smaller tissue fragments, such as into 2 or more tissue fragments, such as 5 or more, such as 10 or more, such as 25 or more, such as 50 or more and including breaking up and separating a biological tissue sample into 100 or more tissue fragments. In embodiments, a given biological tissue sample is considered dissociated, if following dissociation, 2 or more, such as 5 or more, such as 10 or more, such as 25 or more, such as 50 or more, such as 100 or more tissue fragments which were originally stably associated with each other are no longer stably associated with other, i.e., they can be freely moved relative to each other. In certain embodiments, methods include breaking up an organ or tissue in order to collect the smaller components which collectively make up the organ or tissue.

As used herein, the term "biological tissue sample" is used in its conventional sense to refer to a whole organism, plant, fungi or a subset of tissues or component parts of the organism. Biological tissue samples may be obtained from an in vitro source (e.g., tissue grown in laboratory culture) or from an in vivo source (e.g., a mammalian subject, a human subject, etc.). In some embodiments, the tissue sample is obtained from an in vitro source. In some embodiments, the biological tissue sample is obtained from an in vivo source, where in some instances, tissues derived from a subject are cultured, stored, or manipulated prior to evaluation. In vivo sources include living multi-cellular organisms and can yield non-diagnostic or diagnostic tissue samples.

In certain embodiments the source of the tissue sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Biological tissue samples may include tissue from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried out on samples from other animal subjects (that is, in "non-human subjects") such as, but not limited to, birds, mice, rats, dogs, cats, livestock and horses.

In some embodiments, biological tissue samples include tissue from a component part of a human subject, such as organs, including but not limited to integumentary tissue (e.g. sections of the skin), oral tissue (e.g., buccal, tongue, palatal, gums), respiratory tissue (e.g., pharynx, larynx, trachea, bronchi, lungs, diaphragm) gastrointestinal tissue (e.g., esophagus, stomach, liver, gallbladder, pancreas, intestines, colon, rectum and anus.), cardiovascular tissue (e.g., heart, blood vessels), endocrine tissue (e.g., hypothalamus, pituitary gland, pineal body or pineal gland, thyroid, parathyroids, adrenal glands) and genitourinary tissue (kidneys, ureters, bladder, urethra, ovaries, fallopian tubes, uterus, vagina, mammary glands, testes, vas deferens, seminal vesicles, prostate, penis), muscular tissue, nervous tissue (e.g., brain, spinal cord, nerves) as well as soft skeletal tissue (cartilage, ligaments, tendons). Biological samples may be any type of organismic tissue, including both healthy and diseased tissue (e.g., cancerous, malignant, necrotic, etc.)

Tissue dissociator devices of interest may be configured to dissociate biological tissue samples of varying size, depending on the type of tissue and size of housing (as described in greater detail below) where in some instances the length of biological tissue samples may range from 1 cm to 50 cm, such as from 2.5 cm to 45 cm, such as from 5 cm to 40 cm, such as from 7.5 cm to 35 cm and including from 10 cm to 25 cm and the width of biological tissue samples may range from 1 cm to 50 cm, such as from 2.5 cm to 45 cm, such as from 5 cm to 40 cm, such as from 7.5 cm to 35 cm and including from 10 cm to 25 cm. The thickness of biological tissue samples may also vary, ranging from 0.001 mm to 50 mm, such as from 0.005 mm to 25 mm, such as from 0.01 mm to 15 mm, such as from 0.05 mm to 10 mm and including from 0.1 mm to 5 mm. For example, tissue dissociator devices of interest may be configured to dissociate biological tissue samples having a surface area ranging from 0.01 to 100 $cm^2$, such as 0.05 to 50 $cm^2$, such as 0.1 to 25 $cm^2$, such as 0.5 to 15 $cm^2$, such as 0.75 to 10 $cm^2$, such as 1 to 7.5 $cm^2$, and including 2 to 5 $cm^2$. The subject tissue dissociators may be configured to dissociate biological tissue samples having a volume ranging from 0.01 to 100 $cm^3$, such as 0.02 to 50 $cm^3$, such as 0.05 to 25 $cm^3$, such as 0.1 to 15 $cm^3$, such as 0.5 to 10 $cm^3$, such as 0.75 to 7.5 $cm^3$, and including 1 to 5 $cm^3$.

In certain embodiments, the biological tissue sample is a specimen that has been preloaded into a dissociator housing and is stored in the housing for a predetermined period of time before the biological tissue sample is dissociated. For example, the biological tissue sample may preloaded into a dissociator housing and frozen in a freezer. The amount of time the biological tissue sample is stored before dissociating the biological tissue sample may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the biological tissue sample into the dissociator housing 240 hours or more before dissociating the biological tissue sample or may range such as from 0.1 hours to 240 hours before dissociating the biological tissue sample, such as from 0.5 hours to 216 hours, such as from 1 hour to 192 hours and including from 5 hours to 168 hours before disrupting the biological tissue sample. For example, the biological tissue sample may be preloaded into a dissociator housing at a remote location (e.g., at home using an at-home kit or in a physician's office) and sent to a laboratory for processing in accordance with the subject methods. By "remote location" is meant a location other than the location at which the tissue sample is obtained and preloaded into the container. For example, a remote location could be another location (e.g. office, lab, etc.) in the same city, another location in a different city, another location in a different state, another location in a different country, etc., relative to the location of the tissue dissociator device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

As summarized above, tissue dissociators according to certain embodiments include a housing, a cutting blade positioned at a distal end of the housing and a tissue actuator that is configured to be displaced along a longitudinal axis within the housing. The housing has a distal end and a proximal end with walls between the distal end and proximal end that together form an inner chamber within the housing that is configured to receive one or more biological tissue samples. In some embodiments, the outer walls of the housing and inner chamber have the same cross-sectional shape where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. For example, both the outer walls of the housing and the inner chamber may have circular or oval cross sections or both the outer walls of the housing and the inner chamber may have polygonal (e.g., octagonal) cross sections. In other embodiments, the outer walls of the housing and inner chamber within the housing have different cross-sectional shapes (e.g., housing having a circular cross-section and inner chamber having a square or polygonal cross-section)

Depending on the amount and type of tissue sample being processed, the size of the inner chamber of the housing may vary, where in some instances the length of the inner chamber of the housing may range from 1 cm to 50 cm, such as from 2.5 cm to 45 cm, such as from 5 cm to 40 cm, such as from 7.5 cm to 35 cm and including from 10 cm to 25 cm and the width of the inner chamber of the housing may range from 1 cm to 50 cm, such as from 2.5 cm to 45 cm, such as from 5 cm to 40 cm, such as from 7.5 cm to 35 cm and including from 10 cm to 25 cm. Where the inner chamber of the housing has a cylindrical cross-section, the diameter may vary, in some embodiments, ranging from 1 cm to 10 cm, such as from 2 cm to 9 cm, such as from 3 cm to 8 cm and including from 4 cm to 7 cm. Accordingly, the volume of the inner chamber within the housing may vary, ranging from 0.01 to 100 $cm^3$, such as 0.05 to 50 $cm^3$, such as 0.1 to 25 $cm^3$, such as 0.5 to 15 $cm^3$, such as 0.75 to 10 $cm^3$, such as 1 to 7.5 $cm^3$, and including 2 to 5 $cm^3$.

In some embodiments, the tissue dissociator housing includes a proximal cylindrical portion defining a longitudinal axis and a distal frustoconical portion which terminates in an orifice that is transverse to the longitudinal axis of the housing. The length of the proximal cylindrical portion (as measured along the longitudinal axis) may vary ranging from 1 cm to 25 cm, such as from 2.5 cm to 22.5 cm, such as from 5 cm to 20 cm and including from 7.5 cm to 15 cm. The length of the distal frustoconical portion (as measured along the longitudinal axis) may also vary, ranging from 1 cm to 5 cm, such as from 1.5 cm to 4.5 cm, such as from 2 cm to 4 cm and including from 2 cm to 3 cm. Depending on the type of biological tissue sample (e.g., hard tissue, soft tissue), the angle of the frustoconical walls relative to the longitudinal axis of the housing may vary, in certain embodiments, ranging from 120° to 160° such as at an angle which ranges from 125° and 155°, such as from 130° and 150° and including an angle which ranges from 135° and 145°.

As described in greater detail below, a tissue actuator may be displaced along a longitudinal axis within the inner chamber of the housing in discrete increments. Where the tissue actuator is displaced in discrete increments, in some embodiments, the inner chamber of the housing may include one or more notches or protrusions which provide predetermined increments for displacing the tissue actuator within the housing. For example, the inner chamber of the housing may include 2 or more notches or protrusions, such as 3 or more notches or protrusions, such as 4 or more notches or protrusions, such as 5 or more notches or protrusions and including 10 or more notches.

In some embodiments, the inner chamber of the housing has threaded walls and is configured to be screw threaded with the outer walls of the tissue actuator. All or part of the walls of the inner chamber may be threaded, such as 10% or more of the length of the inner chamber, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the entire length (i.e., 100%) of inner chamber of the housing is threaded.

The housing may be formed from any suitable material including, but not limited to, glass, metal or plastic, such as a flexible or rigid plastic, polymeric or thermoplastic materials. For example, suitable polymeric plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the housing is formed from a polyester, where polyesters of interest may include, but are not limited to, housings made of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); Mylar™.

In some embodiments, tissue dissociators of interest are configured to be placed inside and releasably attached to a container. The term "releasably" is used herein in its conventional sense to mean that the tissue dissociator can be freely detached from and re-attached to the container. All or part of the tissue dissociator housing may be configured to fit inside of the container, such as 10% or more, such as 25% or more, such as 50% or more, such as 75% or more, such as 90% or more and including 95% or more of the tissue dissociator housing may be configured to fit within the container. In certain embodiments, the entire tissue dissociator housing is configured to be placed within a container.

In these embodiments, the tissue dissociator may be configured to be attached to a container at the proximal end of the housing, the distal end of the housing, at a positioned between the distal and proximal ends of the housing or any combination thereof. In some instances, the tissue dissociator is configured to be releasably attached at the proximal end of the housing. In other instances, the tissue dissociator is configured to be releasably attached at the distal end of the housing. In certain embodiments, the proximal end of the tissue dissociator housing is configured to be releasably attached to the opening of the container. Where the tissue dissociator is configured to be releasably attached to a container, the housing may include one or more fasteners for attaching the dissociator to the container. Suitable fasteners may include, but are not limited to, hook and loop fasteners, latches, notches, grooves, pins, tethers, hinges, Velcro, non-permanent adhesives or a combination thereof.

In certain instances, the outer wall of the tissue dissociator housing is threaded and is configured to be screw threaded with the inner wall of the container. Depending on the type of container employed, all or part of the outer wall of tissue dissociator housing may be threaded, such as 10% or more of the length of the outer wall of tissue dissociator housing, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the entire length (i.e., 100%) of outer wall of tissue dissociator housing is threaded.

In some embodiments, tissue dissociators of interest include a cap configured to connect the proximal end of the housing to the container. For example, the cap may be a screw cap, a snap-on cap or a cap which connects the tissue dissociator housing and the container by a permanent, semi-permanent or non-permanent adhesive. In certain instances, the cap forms a fluidic seal between the tissue dissociator housing and the container.

Containers of interest may vary and may include but are not limited to a blood collection tube, test tube, centrifuge tube, culture tube, falcon tube, microtube, Eppendorf tube, specimen collection container, specimen transport container, petri dish and syringe. In some embodiments, the container is a syringe barrel and tissue dissociators of interest include a syringe barrel; a housing placed inside of the syringe barrel, the housing having a distal end and a proximal end; a cutting blade positioned at the distal end of the housing; and a tissue actuator configured to be displaced along a longitudinal axis within the housing. In other embodiments, the container is a centrifuge tube and tissue dissociators of interest include a centrifuge tube; a housing placed inside of the centrifuge tube, the housing having a distal end and a proximal end; a cutting blade positioned at the distal end of the housing; and a tissue actuator configured to be displaced along a longitudinal axis within the housing.

Figure 1B:
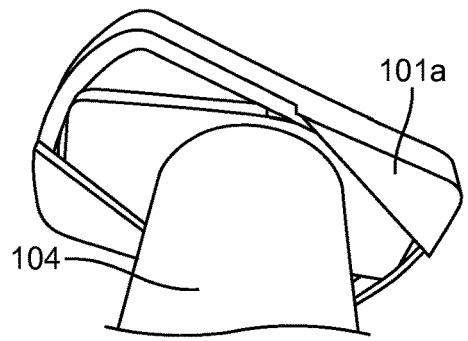
FIG. 1B depict releasably attaching a tissue dissociator to a container according to certain embodiments.

For example, FIG. 1A illustrates a tissue dissociator configured to be placed inside and releasably attached to a syringe according to certain embodiments of the present disclosure. The tissue dissociator includes housing 101, cutting blade 102 and tissue actuator 103, where housing 101 is configured to fit within syringe barrel 104. Housing 101 is inserted completely into syringe barrel 104 and the proximal end of housing 101 is releasably attached to the opening of syringe barrel 104 with fastener 101a. The attachment of the proximal end of housing 101 to the opening of syringe barrel 104 with fastener 101a is shown in greater detail in FIG. 1B which shows the end of syringe barrel 104 fit and lock within faster 101a by twisting the housing to hook the proximal end of the housing to the opening end of syringe barrel 104.

In embodiments of the present disclosure, a cutting blade is positioned at a distal end of the housing. As described above, the cutting blade is configured such that pressing the biological tissue sample against the cutting blade is sufficient to dissociate the tissue into a plurality of tissue fragments. In some embodiments, the cutting blade includes 1 or more blades, such as 2 or more blades, such as 3 or more blades, such as 5 or more blades, such as 10 or more blades and including 25 or more blades. Depending on the shape of the dissociated tissue fragments desired, the configuration of the cutting blade may vary. In some instances, the cutting blade includes a single blade traversing the distal end of the housing. For instance, in one example the single blade is positioned across the midline of the distal end of the housing. In another example, the single blade is positioned a predetermined distance from the midline of the distal end of the housing, such as 1 mm or more from the midline of the housing, such as 2 mm or more, such as 3 mm or more, such as 5 mm or more, such as 7 mm or more and including 10 mm or more from the midline of the distal end of the housing.

In some embodiments, the cutting blade is configured as an array of blades, such as a plurality of blades arranged in parallel rows. For example, the cutting blade may be arranged in 2 parallel rows or more, such as 3 parallel rows or more, such as 4 or parallel rows or more, such as 5 parallel rows or more, such as 10 parallel rows or more, such as 15 parallel rows or more, such as 25 parallel rows or more and including 50 parallel rows or more. The distance between each blade may vary, depending the size of dissociated tissue fragments desired and may be 0.01 mm or greater, such as 0.05 mm or greater, such as 0.1 mm or greater, such as 0.5 mm or greater, such as 1 mm or greater, such as 1.5 mm or greater, such as 2 mm or greater, such as 3 mm or greater, such as 5 mm or greater and including a distance between blades of 10 mm or greater. The distance between each row may be the same, different or some combination thereof. In some instances, the distance between each blade row is the same. In other instances, the distance between each blade row is different. In yet other instances, a first portion of the blade rows are positioned equidistant from each other while a second portion of blade rows are positioned at varying distances from each other.

In other embodiments, the cutting blade is configured as a plurality of concentrically-arranged ring-shaped blades, such as 2 concentrically-arranged ring-shaped blades or more, such as 3 concentrically-arranged ring-shaped blades or more, such as 5 concentrically-arranged ring-shaped blades or more, such as 10 concentrically-arranged ring-shaped blades or more, such as 25 concentrically-arranged ring-shaped blades or more and including 50 concentrically-arranged ring-shaped blades or more. The distance between each blade may vary, such as 0.01 mm or greater, such as 0.05 mm or greater, such as 0.1 mm or greater, such as 0.5 mm or greater, such as 1 mm or greater, such as 1.5 mm or greater, such as 2 mm or greater, such as 3 mm or greater, such as 5 mm or greater and including a distance between blades of 10 mm or greater. The distance between each blade may be the same, different or some combination thereof. In some instances, the distance between each blade is the same. In other instances, the distance between each blade is different. In yet other instances, a first portion of the blades are positioned equidistant from each other while a second portion of blades rows are positioned at varying distances from each other.

In certain embodiments, the cutting blade has a grid configuration (i.e., the cutting blade has a planar arrangement of rectilinear intersecting cutting surfaces, such as e.g., cutting surfaces in the shape of squares, rectangles or curvilinear shapes). Each unit (e.g., square, rectangle) of the grid-shaped cutting blades of interest may be congruent or incongruent or a combination thereof. Depending on the size of the cutting blade and size of dissociated tissue desired, the area of each unit in grid-shaped cutting blades may vary, ranging from 0.01 mm$^2$ to 100 mm$^2$, such as 0.1 mm$^2$ to 90 mm$^2$, such as 0.5 mm$^2$ to 80 mm$^2$, such as 0.75 mm$^2$ to 70 mm$^2$, such as 1 mm$^2$ to 60 mm$^2$, and including 2 mm$^2$ to 50 mm$^2$. In certain instances, cutting blades of interest having a grid configuration are mesh screens. The mesh screen may be any convenient sized mesh screen, such as a 2-mesh screen or smaller, such as a 4-mesh screen or smaller, such as a 10-mesh screen or smaller, such as a 20-mesh screen or smaller, such as a 30-mesh screen or smaller, such as a 40-mesh screen or smaller, and including a 60-mesh screen or smaller.

In some embodiments, the subject tissue dissociator is configured to dissociate a biological tissue sample into a plurality of components having substantially the same size and shape. By substantially the same size and shape is meant that the subject tissue dissociators are configured to dissociate a biological tissue sample into tissue fragments which vary in shape or size by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into tissue fragments which vary in shape or size which vary by 0.01% or less.

For example, the cutting blade may be configured to dissociate the biological tissue sample into a plurality of tissue fragments which vary in size by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into a plurality of tissue fragments which vary in size by 0.01% or less. In certain instances, the cutting blade is configured to dissociate a biological tissue sample into a plurality of tissue fragments that have identical sizes.

In some embodiments, the cutting blade is configured to dissociate a biological tissue sample into tissue fragments which vary in shape by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into tissue fragments which vary in shape by 0.01% or less. In certain instances, the cutting blade is configured to dissociate a biological tissue sample into a plurality of tissue fragments that have identical shape.

The cutting blade is positioned at the distal end of the housing. In some embodiments, the cutting blade is an integrated part of the housing, including where the cutting blade is soldered, welded or affixed to the housing using a permanent adhesive. In other embodiments, the cutting blade is releasably attached to the housing. By "releasably" is meant that the cutting blade can be freely detached from and re-attached to the distal end of the housing. Where the cutting blade is releasably attached to the housing, the cutting blade may be non-permanently fastened to the housing by any convenient attachment protocol, including but not limited to a hook and loop fastener, a latch, a notch, a groove, a pin, a tether, a hinge, Velcro, non-permanent adhesive, a threaded screw, or a combination thereof. In certain instances, the cutting blade includes a threaded outer wall and is screw threaded with the internal walls of the housing.

Figures 2A, 2B:
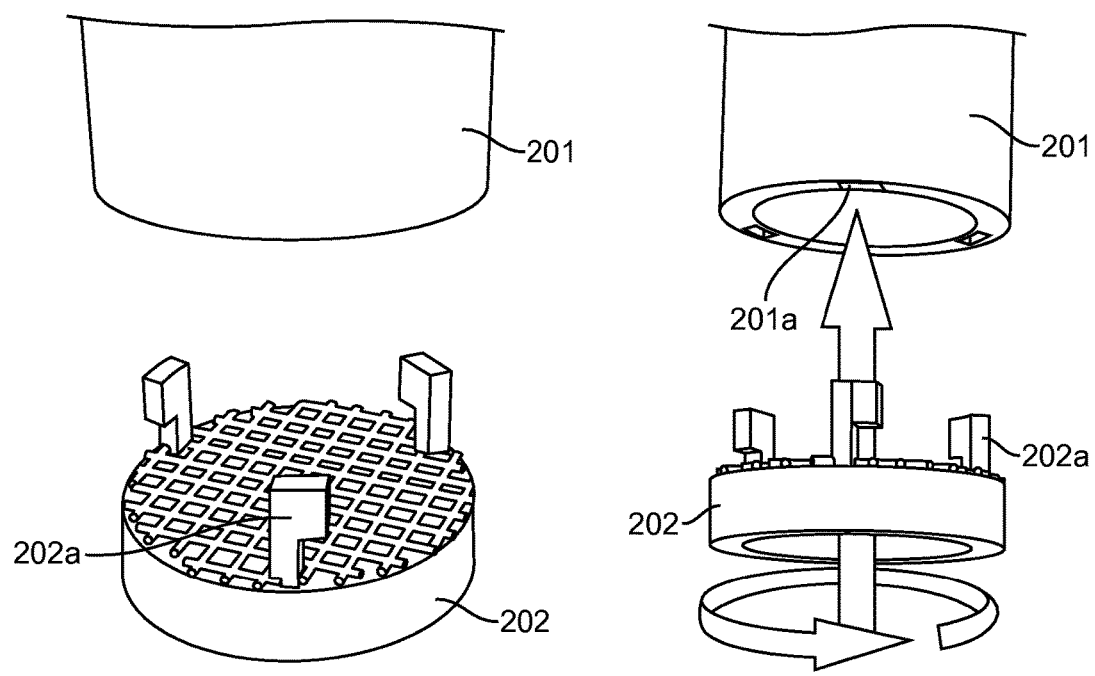
FIG. 2A depicts a cutting blade that is configured to be releasably attached to a tissue dissociator housing according certain embodiments.
FIG. 2B depicts attaching a cutting blade to a tissue dissociator housing according to certain embodiments.

FIGS. 2A and 2B illustrate releasably attaching a cutting blade to the tissue dissociator housing according certain embodiments. FIG. 2A shows cutting blade 202 before attachment to the distal end of housing 201. Cutting blade 202 includes fasteners 202a which are configured to fit into notches within the distal end of housing 201. FIG. 2B shows attaching cutting blade 202 to the distal end of housing 201 by inserting fasteners 202a into notches 201a and turning to secure the cutting blade to the distal end of the housing.

In certain embodiments, the cutting blade includes one or more aligners for maintaining alignment with the tissue actuator. For example, the cutting blade may be a planar grid and include one or more alignment holes for aligning with one or more pins positioned at the distal end of the tissue actuator. For example, the cutting blade may include 1 or more alignment holes, such as 2 or more alignment holes, such as 3 or more alignment holes and including 4 or more alignment holes. The alignment holes for aligning the cutting bladed with the proximal end of the tissue actuator may be positioned at any convenient location along the plane of the cutting blade. For example, one or more alignment holes may be positioned at the center of the cutting blade. In other embodiments, the alignment holes may be positioned along the peripheral edge of the cutting blade. Where more than one alignment hole is positioned along the peripheral edge of the cutting blade, the holes may be equidistant or may be spaced at differing distances from each other. Alignment holes in the plane of the cutting blade may have any suitable cross-sectional shape depending on the alignment pin at the distal end of the tissue actuator. For example, the cross-sectional shape may include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. Each alignment hole may have the same or different cross-sectional shape, as desired.

In certain embodiments, the cutting blade may include or is incorporated into a stripper plate. In these embodiments, the stripper plate is configured to remove and retain dissociated tissue from the tines of the tissue actuator after passing the tissue through the cutting blade and retracting the tissue actuator. For example, the stripper plate may be configured to retain 90% or more of the dissociated tissue passed through the cutting blade, such as 95% or more, such as 97% or more, such as 99% or more, such 99.5% or more and including 99.9% or more. In certain instances, the stripper plate is configured to remove all (i.e., 100% of the dissociated tissue that is passed through the cutting blades. In other words, when the tissue is passed through the cutting blade and the tissue actuator is retracted, the stripper plate is configured to ensure that little, if any, tissue remains on the tines of the tissue actuator.

The stripper plate may be physically coupled to the cutting bladed, such as by a fastener (e.g., hook and loop fasteners, latches, notches, grooves, pins, tethers, hinges, Velcro) or by a permanent or non-permanent adhesive or a combination thereof. In other embodiments, the cutting blade is incorporated into the stripper plate where the stripper plate is both configured to dissociate the tissue contacted when pressed through with the tissue actuator and to remove and retain the tissue from the tines of the tissue actuator.

In some embodiments, the cutting blade is reusable. By "reusable" is meant that the cutting is capable of more than a single use where there is little to no degradation or reduction in performance by the cutting blade after each use. As such, cutting blades in the subject tissue dissociators may be reused 1 more or times, such as 2 or more times, such as 3 or more times, such as 5 or more times, such as 10 or more times, such as 25 or more times, such as 50 or more times and including 100 or more times.

In embodiments, cutting blades show little to no degradation or reduction in performance after each use. The subject cutting blades degrade by 5% or less during each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including degrading by 0.1% or less during each use. In certain embodiments, there is no (i.e., 0%) degradation of the cutting blades after each use. Accordingly, the performance of the cutting blades is reduced by 5% or less after each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including a reduction in performance by 0.1% or less after each use. In certain embodiments, the performance of the cutting blades is entirely unaffected by each use.

Where the cutting blades are reused, methods may further include washing the cutting blades after use or prior to subsequent use, as described in greater detail below. The cutting blades may be washed by any convenient protocol, such as by washing with a solvent, using heat, electromagnetic radiation (e.g., ultraviolet light) or by ultrasound, among other washing protocols.

As summarized above, the subject tissue dissociators include a tissue actuator configured to be displaced along a longitudinal axis within the housing. The term "displace" refers to moving the tissue actuator within the housing in a manner sufficient to bring the biological tissue sample into contact with and to press the biological tissue sample against the cutting blades to dissociate the tissue into a plurality of tissue fragments. In embodiments, the subject tissue dissociator is configured to be displaced along the longitudinal axis within the housing and can be displaced along all or part of the length of the inner chamber of the housing, such as 25% or more of the length of the housing, such as 35% or more, such as 50% or more, such as 60% or more, such as 75% or more, such as 90% or more, such as 95% or more, such as 97% or more and including 99% or more of the length of the housing. In certain embodiments, the tissue actuator can be displaced along the entire (i.e., 100%) length of the housing.

In some embodiments, the tissue actuator is configured to be displaced in a back-and-forth motion within the housing, such as moving from a distal end to a proximal end within the housing and back from the proximal end to the distal end within the housing. For example, the tissue actuator is configured to be displaced in a back-and-forth motion along 25% or more of the length of the housing, such as 35% or more, such as 50% or more, such as 60% or more, such as 75% or more, such as 90% or more, such as 95% or more, such as 97% or more and including 99% or more of the length of the housing. In certain embodiments, the tissue actuator can be displaced in a back-and-forth motion along the entire (i.e., 100%) length of the housing.

The cross-sectional shape of the tissue actuator may vary, depending on the shape of the inner chamber within the housing, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the tissue actuator and the inner chamber of the housing have the same cross-sectional shape. For example, both the tissue actuator and the inner chamber of the housing may have circular or oval cross sections or both the tissue actuator and the inner chamber of the housing may have a polygonal (e.g., octagonal) cross section. In other embodiments, the tissue actuator and inner chamber within the housing have different cross-sectional shapes. For example, the tissue actuator may have a curvilinear cross section and the inner chamber of the housing may have a polygonal cross section or the tissue actuator may have a polygonal cross section and the inner chamber of the housing may have a curvilinear cross section.

Depending on the amount and type of tissue sample being processed and size of the inner chamber of the housing, the dimensions of the tissue actuator may vary where in some instances the length of tissue actuator may range from 1 cm to 50 cm, such as from 2.5 cm to 45 cm, such as from 5 cm to 40 cm, such as from 7.5 cm to 35 cm and including from 10 cm to 25 cm and the width of the tissue actuator may range from 1 cm to 50 cm, such as from 2.5 cm to 45 cm, such as from 5 cm to 40 cm, such as from 7.5 cm to 35 cm and including from 10 cm to 25 cm. Where the tissue actuator has a cylindrical cross-section, the diameter of the of the tissue actuator may vary, in some embodiments, ranging from 1 cm to 10 cm, such as from 2 cm to 9 cm, such as from 3 cm to 8 cm and including from 4 cm to 7 cm.

In some embodiments, all or part of tissue actuator has a cross-section that is substantially the same size as the inner chamber of the housing. In other words, the outer walls of the tissue actuator are flush with the inner walls of the housing. For example, 5% or more of the length of the tissue actuator may have a cross section that is substantially the same size as the inner chamber of the housing, such as 10% or more, such as 25% or more, such as 50% or more, such as 75% or more, such as 90% or more and including 95% or more of the length of the tissue actuator may have a cross section that is substantially the same size as the inner chamber of the housing. In certain embodiments, the entire length of the tissue actuator has a cross section that is substantially the same size as the inner chamber of the housing. In some instances, the outer walls of the tissue actuator form a fluidic seal with the inner chamber of the housing. The term "fluidic seal" is used herein in its conventional sense to refer to the absence of space sufficient for fluid to flow between the outer walls of the tissue actuator and the inner chamber of the housing. For instance, the distal portion of the tissue actuator may form a fluidic seal with the inner chamber of the housing. In other instances, the entire length of the tissue actuator forms a fluidic seal with the inner chamber of the housing.

As described in greater detail below, tissue is pressed into contact and through the cutting blade by the distal end of the tissue actuator. As such, the distal end of the tissue actuator may be configured for contacting the biological tissue sample. In some embodiments, the distal end of the actuator is flat. In other embodiments, the distal end of the tissue actuator has a convex shape. In yet other embodiments, the distal end of the tissue actuator includes one or more protrusions for contacting the biological tissue sample.

In certain embodiments, the distal end of the tissue actuator includes one or more tines, such as two or more tines, such as 3 or more tines, such as 5 or more tines, such as 10 or more tines, such as 25 or more tines, such as 50 or more tines and including 100 or more tines. In certain instances, the tines are arranged in a grid configuration. Tines may have dimensions that vary, depending on the cutting blade or type of tissue being dissociated (e.g., varying by thickness, density, etc.). In some embodiments, tines may be 1 mm or greater, such as 1.5 mm or greater, such as 2 mm or greater, such as 3 mm or greater, such as 5 mm or greater, such as 10 mm or greater and including 25 mm or greater. Depending on the spacing between cutting blades, the tines may have a width of 1 mm or greater, such as 2 mm or greater, such as 5 mm or greater and including 10 mm or greater. In certain instances, the distal end of the tissue actuator includes space between tines (i.e., inter-tine spacings). In these instances, the distance between each tine may be 0.5 mm or greater, such as 1 mm or greater, such as 2 mm or greater and including 5 mm or greater.

Tines of interest may have any suitable cross-sectional shape, depending on the shape of the cutting blade and the shape of the dissociated tissue fragments desired. Cross-section shapes of tines of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion.

In some embodiments, the outer walls of the tissue actuator include one or more aligners configured to orient the tissue actuator within the inner chamber of the housing. For example, the outer walls of the tissue actuator may include an alignment protrusion, an alignment rail, an alignment notch, an alignment groove, an alignment slot or a combination thereof. Where the outer walls of the tissue actuator include one or more aligners, the walls of the inner chamber of the housing may also include an aligner, such as an aligner which is complimentary to the aligner on the outer walls of the tissue actuator. For example, where the tissue actuator includes an alignment protrusion, the inner chamber of the housing may include an alignment notch. In another example, where the tissue actuator includes an alignment groove, the inner chamber of the housing may include an alignment rail.

Depending on the displacement of the tissue actuator within the inner chamber of the housing, the size of the aligner may vary. For example, the aligner may extend along all or part of the length of the tissue actuator, such as 10% or more of the length of the tissue actuator, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the aligner extends the entire length (i.e., 100%) of the tissue actuator. Accordingly, in embodiments the length of the aligner may vary ranging from 0.1 cm to 25 cm, such as from 0.5 cm to 22.5 cm, such as from 1 cm to 20 cm, such as from 2.5 cm to 15 cm and including from 5 cm to 10 cm and the width of the aligner may vary ranging from 0.01 cm to 5 cm, such as from 0.05 cm to 2.5 cm, such as from 0.1 cm to 2 cm and including from 0.5 cm to 1.5 cm.

The outer walls of the tissue actuator may include 1 or more aligners, such as 2 or more aligners, such as 3 or more aligners, such as 4 or more aligners and include 5 or more aligners. Where the tissue actuator includes more than one aligner, each aligner may be positioned anywhere on the tissue actuator as desired. For example, an aligner may be positioned at a distal end, a proximal end, between the proximal end and the distal end or a combination thereof. Aligners may be positioned on opposite sides of the tissue actuator, such as two aligners on opposite sides at the distal end of the tissue actuator or two aligners on opposite sides at the proximal end of the tissue actuator. In some embodiments, the tissue actuator includes a first aligner at the distal end and a second aligner at the proximal end.

In certain embodiments, the distal end of the tissue actuator may include one or more aligners which couple with the cutting blade. For example, the distal end of the tissue actuator may include one or more alignment pins which fit through and align the tissue actuator with the cutting blade. The dimensions of the alignment pins may vary, depending on the size of the alignment holes positioned in the cutting blade. In embodiments, the length of the alignment pins may vary ranging from 0.1 cm to 25 cm, such as from 0.5 cm to 22.5 cm, such as from 1 cm to 20 cm, such as from 2.5 cm to 15 cm and including from 5 cm to 10 cm and the width (e.g., diameter) of the alignment may vary ranging from 0.01 cm to 5 cm, such as from 0.05 cm to 2.5 cm, such as from 0.1 cm to 2 cm and including from 0.5 cm to 1.5 cm. Where more than one alignment pin is present, each alignment pin may have one or more of the same dimensions (i.e., length and width) or each alignment pin may have different dimensions. For example, each alignment pin may be the same or different lengths and may have the same or different widths. Alignment pins at the distal end of the tissue actuator may have any suitable cross-sectional shape depending on the alignment hole in the cutting blade. For example, the cross-sectional shape may include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. Each alignment pin may have the same or different cross-sectional shape, as desired.

Depending on the position of the alignment holes in the cutting blade, the alignment pins at the distal end of the tissue actuator may be positioned at any convenient location, such as at the center of the tissue actuator or along the peripheral edge. Where more than one alignment pin is positioned along the peripheral edge of the tissue actuator distal end, the alignment pins may be spaced equidistant or at a varying distances from each other.

As described in greater detail below, the tissue actuator may be displaced along a longitudinal axis within the inner chamber of the housing. In some embodiments, the tissue actuator may be continuously displaced within the inner chamber. In other embodiments, the tissue actuator may be displaced in discrete increments. Where the tissue actuator is displaced in discrete increments, in some embodiments, the tissue actuator may include one or more notches or protrusions which provide predetermined increments for displacing the tissue actuator within the housing. For example, the tissue actuator may include 2 or more notches or protrusions, such as 3 or more notches or protrusions, such as 4 or more notches or protrusions, such as 5 or more notches or protrusions and including 10 or more notches or protrusions.

In some embodiments, the outer walls of the tissue actuator are threaded and configured to be screw threaded with the walls of the inner chamber of the housing. All or part of the outer walls of the tissue actuator may be threaded, such as 10% or more of the length of the tissue actuator, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the entire length (i.e., 100%) of outer walls of the tissue actuator is threaded.

Figure 3:
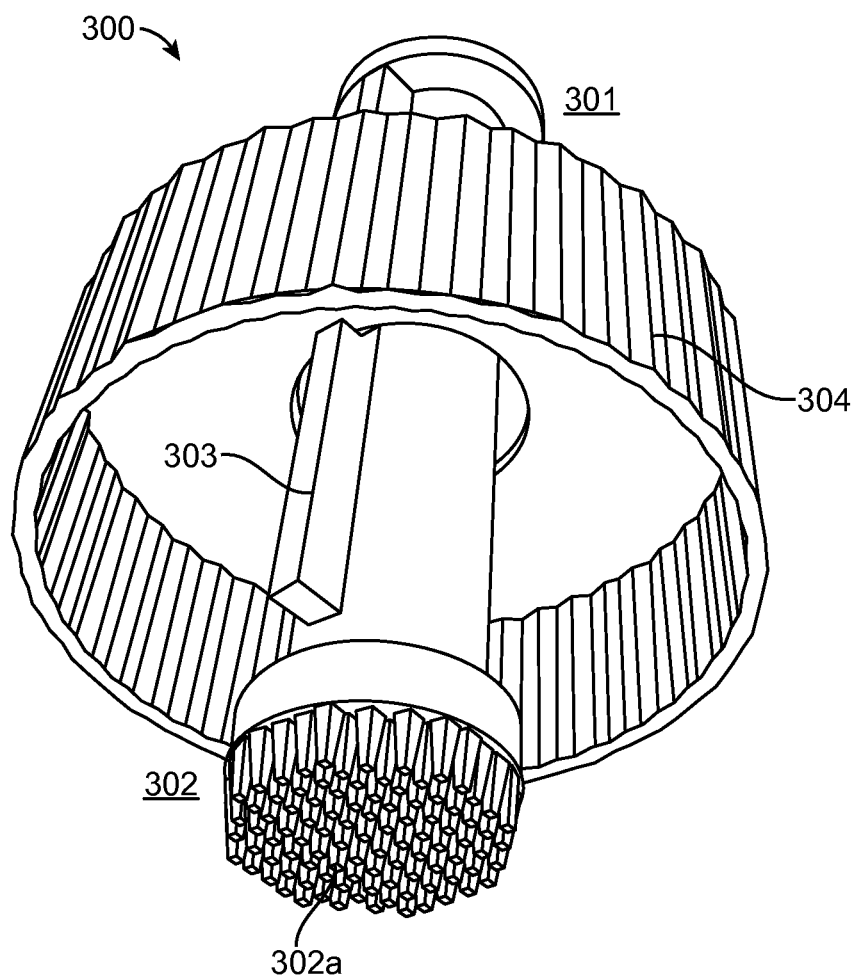
FIG. 3 illustrates aspects of a tissue actuator according to certain embodiments.

FIG. 3 illustrates aspects of tissue actuators according to certain embodiments of the present disclosure. Tissue actuator 300 includes proximal end 301 and distal end 302, which is configured to contact and press a biological tissue sample through cutting blades to dissociate the biological tissue sample into a plurality of tissue fragments. As shown in FIG. 3, distal end 302 of tissue actuator 300 includes an array of tines 302a which are configured to engage with the biological tissue sample. The tines may be configured to fit between the cutting blades when dissociating the biological tissue sample. Tissue actuator 300 also include alignment protrusion 303 configured to orient the tissue actuator within the tissue dissociator housing. Cap 304 is configured to connect the housing of the tissue dissociator to a container.

In certain embodiments, the tissue actuator includes a fluid reservoir within an inner chamber of the tissue actuator. The fluid reservoir within the inner chamber of the tissue actuator may be any suitable shape, in some instances having the same cross-sectional shape as the tissue actuator. For example, the fluid reservoir may have a rectilinear cross-sectional shape, such as a square, rectangle, trapezoid, triangle, hexagon or a curvilinear cross-sectional shape, such as a circle, oval, as well as irregular cross-sectional shapes, such as a parabolic bottom portion coupled to a planar top portion.

The fluid reservoir may extend all or part of the length within the tissue actuator, such as 10% or more of the length within the tissue actuator, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the inner chamber extends the entire length (i.e., 100%) within the tissue actuator.

In some embodiments, the fluid reservoir includes more than one compartment, such as 2 or more compartments, such as 3 or more compartments, such as 4 or more compartments and including 5 or more compartments. Each compartment may be separated by a partition, such as a permeable, semi-permeable or impermeable barrier. In some embodiments, the barrier is a partition having one or more holes such that the each compartment is in fluid communication with one or more of the other compartments. In other embodiments, each compartment is separated by a semi-permeable polymeric membrane.

In certain embodiments, the distal end of the tissue actuator is in fluid communication with the fluid reservoir, such through holes which extend from the reservoir through the distal end of the tissue actuator. Where desired, fluid from within the fluid reservoir may be expelled from the distal end of the tissue actuator by applying a positive pressure within the fluid reservoir. In these embodiments, the distal end of the tissue actuator includes one or more holes which extends from the outer wall at the distal end of the tissue actuator through to the fluid reservoir, such as 2 or more holes, such as 3 or more holes, such as 5 or more holes, such as 10 or more holes, such as 25 or more holes, such as 50 or more holes and including 100 or more holes. In some instances, the holes are arranged in a grid pattern. In certain embodiments, the holes may be interspersed between tines positioned at the distal end of the tissue actuator.

Positive pressure may be applied within the fluid reservoir to expel fluid from the distal end of the tissue actuator by any convenient protocol, such as mechanically with a plunger or hydraulically by pumping air or a gas into the fluid reservoir. In certain embodiments, positive pressure is applied to expel fluid through holes at the distal end of the tissue actuator with a plunger. In these embodiments, the plunger is configured to be displaced along a longitudinal axis within the fluid reservoir. Any convenient liquid may be present in the fluid reservoir, where liquids of interest include, but are not limited to, water and other aqueous liquids, e.g., buffered solutions (such as HEPES, MOPS, PBS, etc.) and the like. The tissue actuator may be displaced along a longitudinal axis within the fluid reservoir continuously or in discrete increments. Where the plunger is displaced in discrete increments, in some embodiments, the fluid reservoir may include one or more notches or protrusions which provide predetermined increments for displacing the plunger within the fluid reservoir. For example, the fluid reservoir may include 2 or more notches or protrusions, such as 3 or more notches or protrusions, such as 4 or more notches or protrusions, such as 5 or more notches or protrusions and including 10 or more notches or protrusions.

Figure 4:
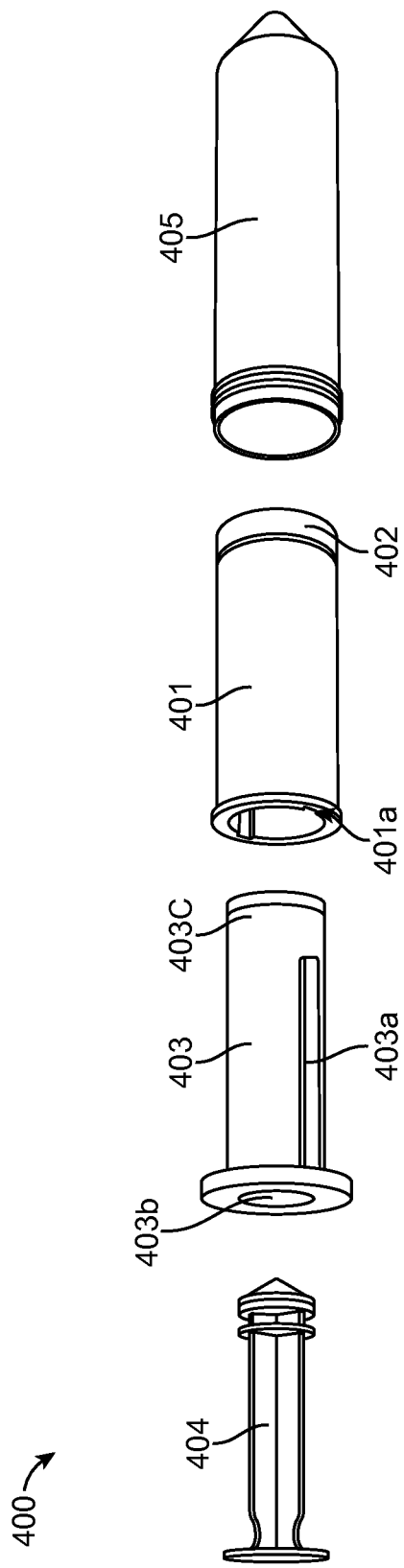
FIG. 4 illustrates an external side view of a tissue dissociator having a tissue actuator which includes a fluid reservoir according to certain embodiments.

FIG. 4 illustrates a side view of a tissue dissociator having a tissue actuator which includes a fluid reservoir according to certain embodiments. Tissue dissociator 400 includes housing 401 having alignment channels 401a. Positioned at the distal end of housing 401 is a cutting blade 402. Tissue actuator 403 fits within the inner chamber of housing 401 and includes alignment protrusions 403a which fit into alignment channels 401a to orient tissue actuator 403 for displacement along a longitudinal axis of housing 401. Tissue actuator 403 includes an inner chamber 403b having a fluid reservoir which is in fluid communication through holes with the distal end of the tissue actuator 403c. At proximal end 403b of the tissue actuator, plunger 404 is inserted to apply positive pressure within the fluid reservoir to expel fluid from the distal end of tissue actuator 403c. The housing may be configured to be placed within container 405.

Figure 5:
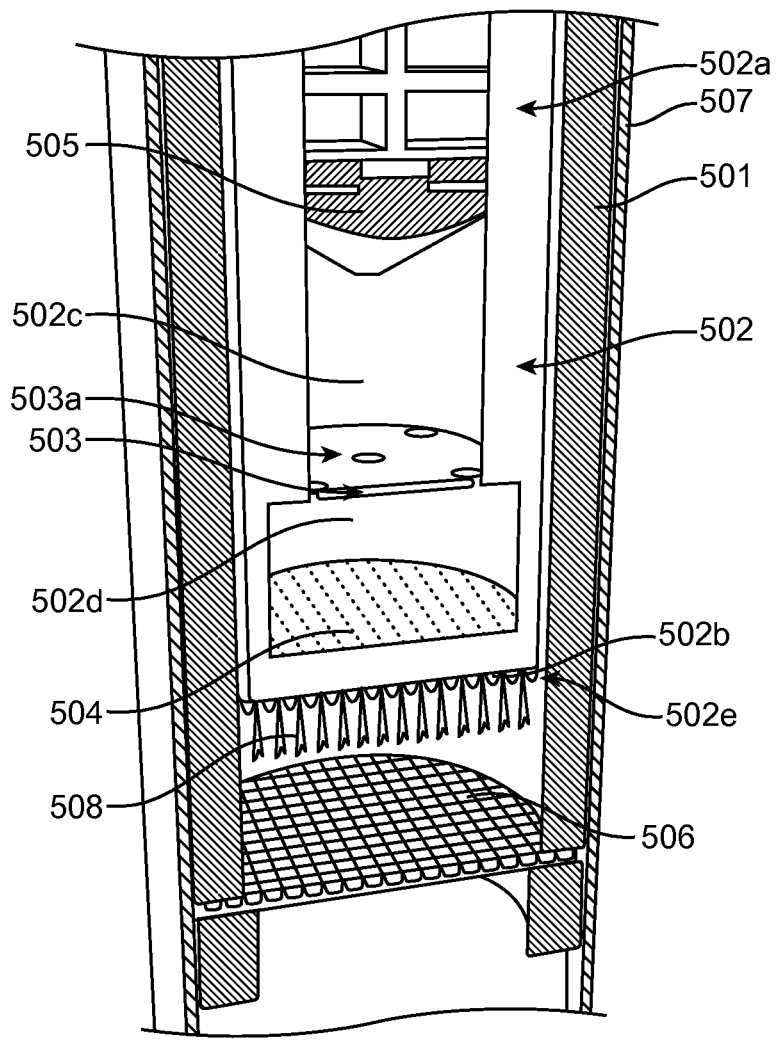
FIG. 5 illustrates an example of a tissue actuator having a fluid reservoir within an inner chamber of the tissue actuator to certain embodiments.

FIG. 5 illustrates an example of a tissue actuator having a fluid reservoir within an inner chamber of the tissue actuator to certain embodiments of the present disclosure. Tissue actuator 502 fits within the inner chamber of tissue dissociator housing 501 and includes a proximal end 502a and a distal end 502b. Tissue actuator 502 includes a fluid reservoir having two compartments 502c and 502d configured to retain a fluid medium. Compartments 502c and 502d are separated by barrier 503 which includes one or more holes 503a such that compartments 502c and 502d are in fluid communication with each other. Tissue actuator 502 includes a plurality of holes 504 in an array configuration such that the fluid reservoir is in fluid communication with the outer wall of distal end 502b. In this example, the outer wall of distal end 502b includes an array of tines 502e and each hole 504 is positioned between tines 502e. Tissue actuator 502 also includes plunger 505 at the proximal end to apply a positive pressure to the first compartment 502c of the fluid reservoir to expel fluid 505 through holes 504 at the distal end of tissue actuator 502. As shown in FIG. 5, fluid expelled 508 through holes 504 at the distal end of tissue actuator 502 can be used to clear or wash biological tissue sample remaining in cutting blade 506. The entire tissue dissociator can be fit, as described above into a container 507 such as a culture tube.

Figure 6:
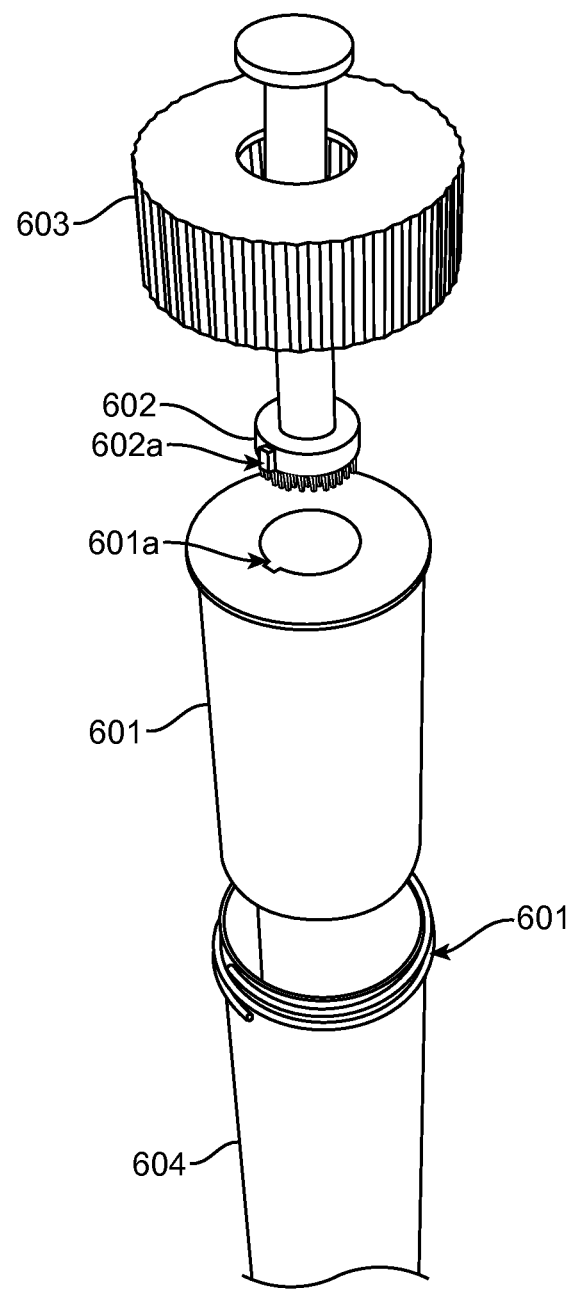
FIG. 6 depicts an exploded view of components of a tissue dissociator according to certain embodiments.

FIGS. 6 and 7 further illustrate various aspects of tissue dissociators according certain embodiments. FIG. 6 is an exploded view of tissue dissociator 600 which includes housing 601 having a distal end and a proximal end, tissue actuator 602 that includes alignment protrusion 602a at the distal end of tissue actuator 602. Alignment protrusion 602a is configured to fit into alignment groove 601b which extends the entire length of the inner chamber 601a within housing 601. As illustrated in FIG. 6, housing 601 is configured to be placed inside of container 604 and connected by screw thread with cap 603.

Figure 7A:
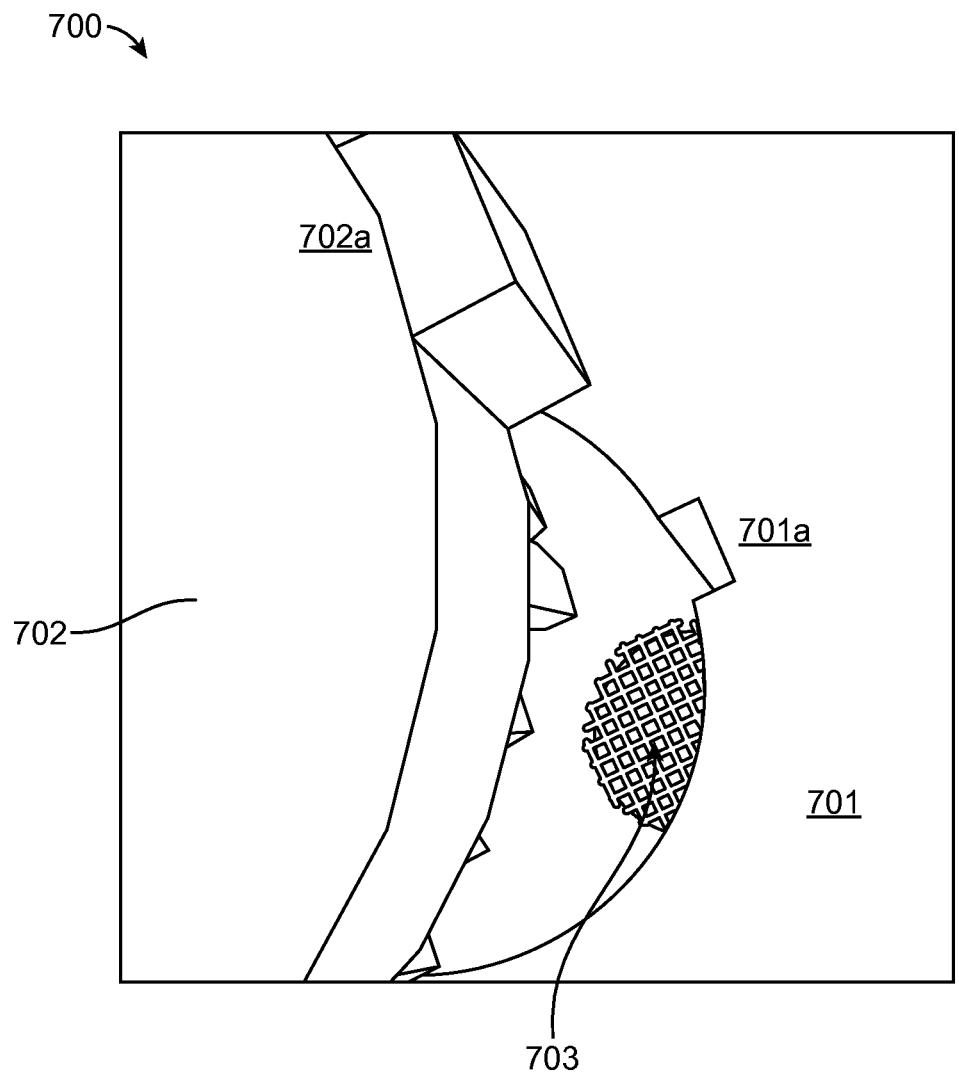
FIG. 7A illustrates a top view of components of a tissue dissociator according to certain embodiments.
Figure 7B:
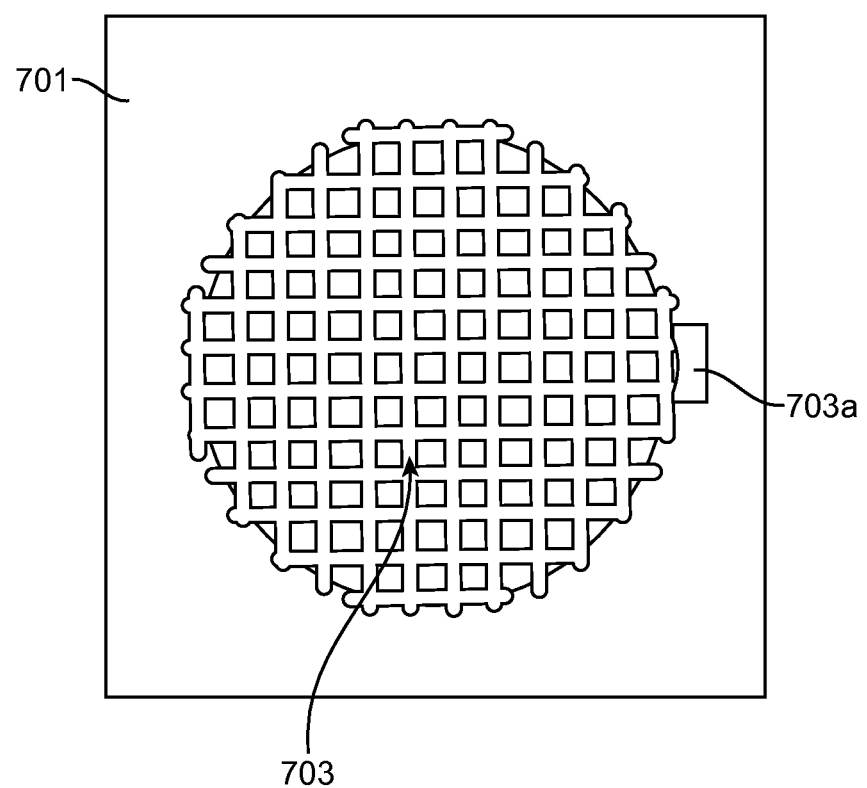
FIG. 7B illustrates a top view of components of a tissue dissociator according to certain embodiments

FIG. 7A illustrates a top view of a tissue dissociator 700 according to certain aspects of the present disclosure. Tissue dissociator housing 701 includes alignment notch 701a for orienting tissue actuator 702 within the inner chamber of the housing. Tissue actuator 702 includes alignment protrusion 702a that fits into alignment notch 701a so that tissue actuator 702 can be displaced along a fixed longitudinal axis within the inner chamber of housing 701. At the distal end of housing 701 is cutting blade 703 which has a grid configuration. A full view of cutting blade 703 is shown in FIG. 7B which shows the grid configuration of the cutting blade and includes fastener 703a for attaching the cutting blade to the distal end of tissue dissociator housing 701.

Figure 8:
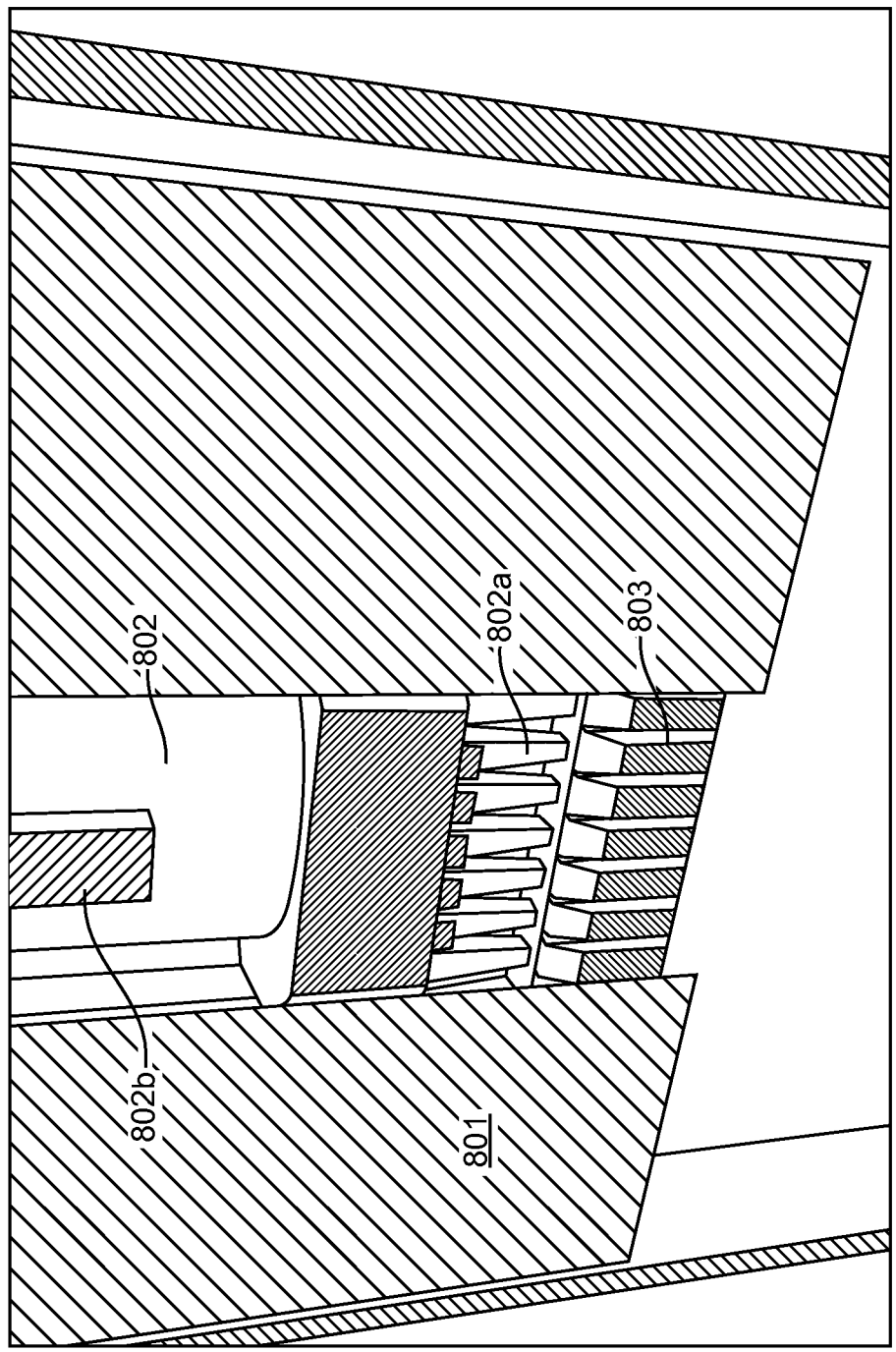
FIG. 8 illustrates a cross-section of a tissue dissociator where the distal end of a tissue actuator is engaged with the cutting blade at the distal end of the housing according to certain embodiments.

FIG. 8 illustrates a cross-section of the tissue dissociator depicting the distal end of tissue actuator 802 engaging with cutting blade 803 in housing 801. As shown in FIG. 8, tines 802a positioned at the distal end of tissue actuator 802 are arranged to fit between the cutting surfaces of cutting blade 803. Here, tissue actuator 802 includes alignment protrusion 802b to orient tissue actuator 802 within the inner chamber of housing 801 so that tines 802a can slide by the cutting surfaces of cutting blade 803 without resistance.

In other embodiments, the tissue dissociator may include the tissue actuator, the housing and a stripper plate. In this embodiment, the tines of the actuator may be circular pins of substantial length, such that prior to insertion of the actuator into the housing element or tissue mincing interface, the stripper plate is loaded onto the tine or pin array and raised all the way to the top. Long guide pins are used to maintain registration of the entire device. Using the guide pins, the actuator is then inserted into the tissue housing and the actuator is depressed all the way down. As the tissue is pressed through the holes in the tissue housing element, the stripper plate is held at the uppermost portion of the pin array. The actuator is then retracted as the stripper plate is held in place effectively stripping any residual tissue off of the pin array. Another feature to this embodiment includes a fluidics element such that once the tissue has been minced and a buffered solution (such as HEPES, MOPS, PBS, etc.) can be introduced under positive pressure by means of a syringe connected tube into the top-most point of the tissue housing element. This cylinder extends down all the way through the apparatus. The terminus of the cylinder is a small protrusion on the underneath side of the housing element. As fluid is applied to the cylinder, a series of slits at the base of the cylinder produce a radial spray of fluid such that the base of the housing element is rinsed and residual tissue is or cellular debris are washed into the receptacle.

Figure 9A:
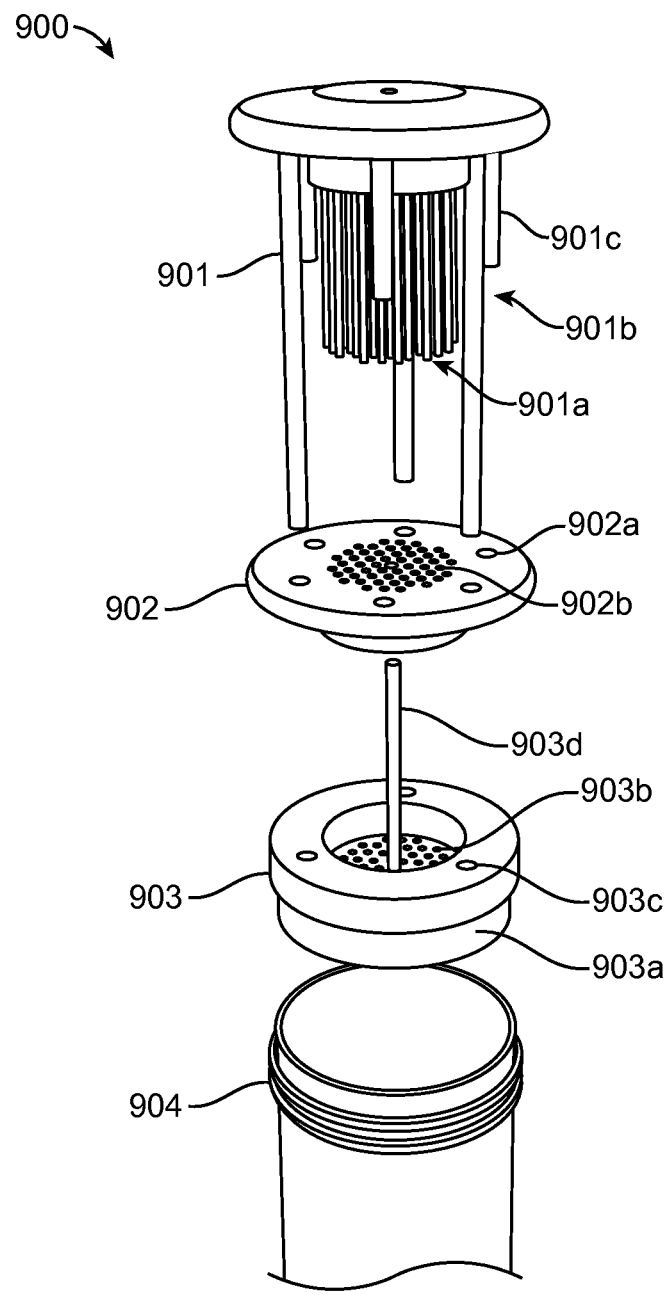
FIG. 9A illustrates a side view of a tissue dissociator having a stripper plate and alignment pins between the stripper plate and tissue actuator according to certain embodiments.

FIG. 9A illustrates a side view of a tissue dissociator having a tissue actuator according to certain embodiments. Tissue dissociator 900 includes an array of pins 901a as well as three major guide pins 901b that aligns the entire device. Three minor guide pins 901c serve to align as well as provide a hard stop to dictate depth of engagement of the actuator. This embodiment also includes a stripper plate 902 which includes an array of holes 902a and 902b through which the actuator pins 901a pass freely as well as guide pin holes through which both sets of guide pins 901*b* and 901*c* pass freely. A tissue housing element 903 is configured with a lip 903*a* such that the housing element securely rests on the edge of the container 904. The housing element 903 also includes a tissue reservoir 903*b* which is where the tissue is placed. The tissue reservoir 903*b* is made up of a platform of holes through which the pin array 901*a* passes through freely. The housing element 903 also includes three holes 903*c* which provide alignment and through which the major guide pins 901*b* pass freely. A long hollow cylinder 903*d* extends up through the entire device and provides a port through which fluid may be applied under positive pressure to the underside of the housing element 903.

Figure 9B:
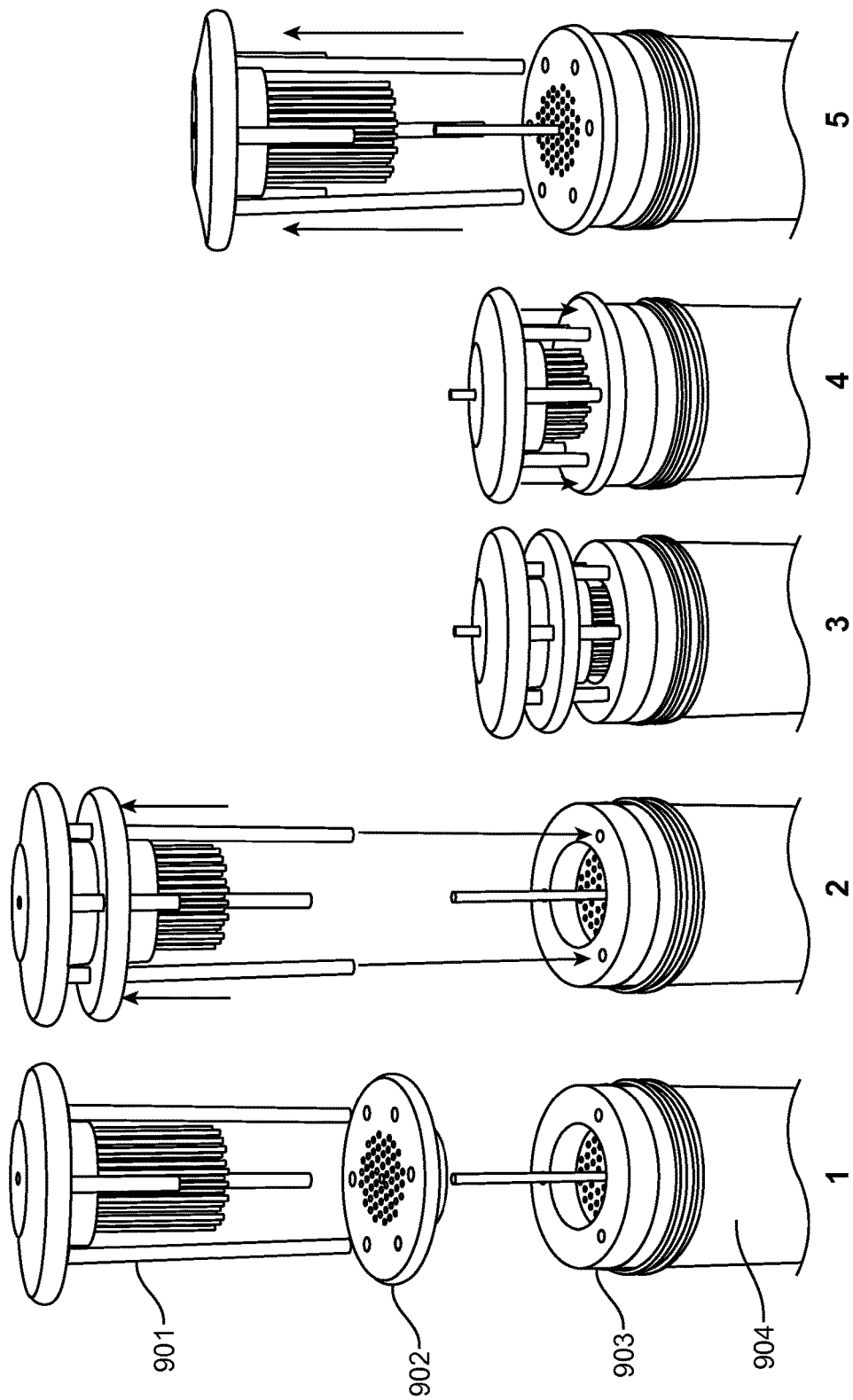
FIG. 9B illustrates step-wise engagement of the tissue actuator with the stripper plate for preparing tissue fragments in a tissue dissociator according to certain embodiments.

FIG. 9B shows the step-wise engagement of the tissue actuator 901, the stripper plate 902, the tissue housing 903 and the container 904. In step 1, the tissue housing is placed on the edge of the container 904. In step 2, the stripper plate 902 is mounted onto the tissue actuator 901 and moved to the upper-most portion of the pin array as the actuator is mounted down into the housing element 903. In step 3, the actuator 901 is pushed down into the housing element 903 until the hard stop is reached such that the pin array fully passes through the holes in the housing element 904. In step 4, the stripper plate 902 is moved downward to its hard stop with the base of the stripper plate 902 resting against the surface of the tissue reservoir inside the housing 903. In step 5, the stripper plate 902 is held in position, as the actuator 901 is retracted.

Figure 9C:
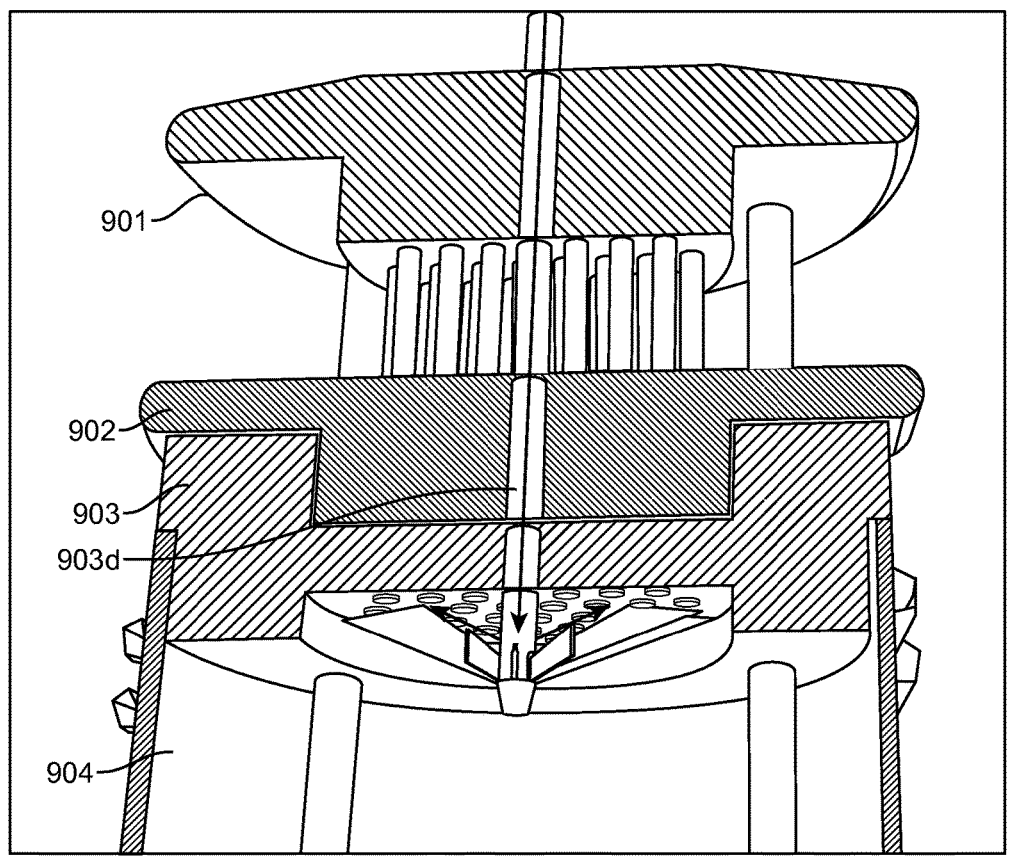
FIG. 9C illustrates a side view of a tissue dissociator having a stripper plate and a conduit for providing fluid to the distal end of the tissue actuator according to certain embodiments.

In FIG. 9C, a detail of the fluidics component of the housing is shown. Once the actuator is fully engaged and the pin array has passed through the holes in the housing 903, a syringe, or some other means of generating positive pressure, can be attached to the upper tip of the hollow cylinder 903*d*. A yellow arrow tracks the path of the buffered solution as it passes under positive pressure down through the cylinder 903*d* down to the base at which point it would generate a radial spray to rinse to rinse the base of the housing element 903.

Methods for Dissociating a Biological Tissue Sample

Aspects of the disclosure also include methods for dissociating a biological tissue sample. Methods according to certain embodiments include: 1) inserting a biological tissue into the housing of a tissue dissociator where the tissue dissociator includes a housing having a distal end and a proximal end, a cutting blade positioned at the distal end of the housing and a tissue actuator configured to be displaced along a longitudinal axis within the housing; and 2) pressing the biological tissue against the cutting blades by displacing the tissue actuator from the proximal end to the distal end of the housing in a manner sufficient to produce a dissociated biological tissue.

In embodiments of the present disclosure, the biological tissue sample may be a whole organism, plant, fungi or a subset of tissues or component parts of the organism. Biological tissue samples may be obtained from an in vitro source (e.g., tissue grown in laboratory culture) or from an in vivo source (e.g., a mammalian subject, a human subject, etc.). In some embodiments, the tissue sample is obtained from an in vitro source. In some embodiments, the tissue sample is obtained from an in vivo source, where in some instances, tissues derived from a subject are cultured, stored, or manipulated prior to evaluation. In vivo sources include living multi-cellular organisms and can yield non-diagnostic or diagnostic tissue samples.

In certain embodiments the source of the tissue sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Biological tissue samples may include tissue from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried out on samples from other animal subjects (that is, in "non-human subjects") such as, but not limited to, birds, mice, rats, dogs, cats, livestock and horses.

In some embodiments, methods include dissociating tissue from a component part of a human subject, such as organs including but not limited to integumentary tissue (e.g. sections of the skin), oral tissue (e.g., buccal, tongue, palatal, gums), respiratory tissue (e.g., pharynx, larynx, trachea, bronchi, lungs, diaphragm) gastrointestinal tissue (e.g., esophagus, stomach, liver, gallbladder, pancreas, intestines, colon, rectum and anus.), cardiovascular tissue (e.g., heart, blood vessels), endocrine tissue (e.g., hypothalamus, pituitary gland, pineal body or pineal gland, thyroid, parathyroids, adrenal glands) and genitourinary tissue (kidneys, ureters, bladder, urethra, ovaries, fallopian tubes, uterus, vagina, mammary glands, testes, vas deferens, seminal vesicles, prostate, penis), muscular tissue, nervous tissue (e.g., brain, spinal cord, nerves) as well as soft skeletal tissue (cartilage, ligaments, tendons). Biological samples may be any type of organismic tissue, including both healthy and diseased tissue (e.g., cancerous, malignant, necrotic, etc.)

The size of tissue dissociated by the subject methods may vary, depending on the type and source of tissue as well as the tissue dissociator employed. For example, the length of biological tissue samples may range from 1 cm to 50 cm, such as from 2.5 cm to 45 cm, such as from 5 cm to 40 cm, such as from 7.5 cm to 35 cm and including from 10 cm to 25 cm and the width of biological tissue samples may range from 1 cm to 50 cm, such as from 2.5 cm to 45 cm, such as from 5 cm to 40 cm, such as from 7.5 cm to 35 cm and including from 10 cm to 25 cm. The thickness of biological tissue samples may also vary, ranging from 0.001 mm to 50 mm, such as from 0.005 mm to 25 mm, such as from 0.01 mm to 15 mm, such as from 0.05 mm to 10 mm and including from 0.1 mm to 5 mm. For example, methods may include dissociating biological tissue samples having a surface area ranging from 0.01 to 100 $cm^2$, such as 0.05 to 50 $cm^2$, such as 0.1 to 25 $cm^2$, such as 0.5 to 15 $cm^2$, such as 0.75 to 10 $cm^2$, such as 1 to 7.5 $cm^2$, and including 2 to 5 $cm^2$. In some embodiments, methods include dissociating biological tissue samples having a volume ranging from 0.01 to 100 $cm^3$, such as 0.05 to 50 $cm^3$, such as 0.1 to 25 $cm^3$, such as 0.5 to 15 $cm^3$, such as 0.75 to 10 $cm^3$, such as 1 to 7.5 $cm^3$, and including 2 to 5 $cm^3$.

In practicing methods according to certain embodiments, a biological tissue sample is inserted into the housing of the tissue dissociator and the biological tissue sample is displaced along a longitudinal axis within the inner chamber of the housing with a tissue actuator and contacted with cutting blades positioned at the distal end of the housing. The tissue actuator may be displaced along all or part of the length inner chamber of the housing to dissociate the biological tissue sample. For example, the tissue actuator may be displaced along 25% or more of the length of the housing to dissociate the biological tissue sample, such as 35% or more, such as 50% or more, such as 60% or more, such as 75% or more, such as 90% or more, such as 95% or more, such as 97% or more and including 99% or more of the length of the housing. In certain embodiments, the tissue actuator is displaced along the entire (i.e., 100%) length of the housing to dissociate the biological tissue sample.

The tissue actuator may be displaced continuously or in discrete increments. In some embodiments, the tissue actuator is displaced continuously. In other embodiments, the tissue actuator is displaced in one or more discrete increments, such as in 2 or more discrete increments, such as 3 or more, such as 4 or more, such as 5 or more, such as 10 or more and including in 25 or more discrete increments. Depending on the size of the tissue dissociator housing as well as the type of biological tissue sample, each discrete increment may vary in length. For example, each discrete increment may be 1 mm or more, such as 2 mm or more, such as 5 mm or more, such as 10 mm or more, such as 25 mm or more and including 50 mm or more.

In certain embodiments, tissue actuator is displaced in a back-and-forth motion along a longitudinal axis within the housing, such as moving from a distal part to a proximal part of the housing and back from the proximal part to the distal part of the housing. In some instances, tissue actuator is displaced in a back-and-forth motion along only a portion of the inner chamber of the housing. For example, the tissue actuator is displaced in a back-and-forth motion along 99% or less of the length of the inner chamber of the housing, such as 95% or less, such as 90% or less, such as 85% or less, such as 80% or less, such as 75% or less, such as 70% or less, such as 65% or more, including displacing the tissue actuator in a back-and-forth motion along 50% or less of the length of the inner chamber of the housing.

Where the tissue actuator is moved in a back-and-forth motion, the movement of the tissue actuator may be repeated one or more times to dissociate the biological tissue sample as desired, such as 2 or more times, such as 5 or more times, such as 10 or more times, such as 15 or more times and including 25 or more times.

Depending on the type of biological tissue sample and size of tissue dissociator employed, the rate that the tissue actuator is displaced within the housing may vary. For example, the tissue actuator may be displaced within the housing at a rate of 1 mm/second or more, such as 2 mm/second or more, such as 3 mm/second or more, such as 5 mm/second or more, such as 10 mm/second or more and including displacing the tissue actuator within the housing at a rate of 25 mm/second or more.

In embodiments, tissue dissociation can be carried out at any suitable temperature so long as the viability of the biological tissue sample and dissociated tissue fragments are preserved as desired. As such, the temperature according to embodiments of the disclosure may vary, such as from −80° C. to 100° C., such as from −75° C. to 75° C., such as from −50° C. to 50° C., such as from −25° C. to 25° C., such as from −10° C. to 10° C., and including from 0° C. to 25° C.

In certain embodiments, methods also include monitoring the plurality tissue fragments produced while dissociating the biological tissue sample. Monitoring dissociation of the biological tissue sample may include assessing the produced plurality of tissue fragments. For example, monitoring dissociation of the biological tissue sample may include evaluating the homogeneity of sizes of the produced tissue fragments. Monitoring dissociation of the biological tissue sample may also include evaluating the homogeneity of the shape of the produced tissue fragments. Any convenient protocol may be employed to monitor dissociation of the biological tissue sample, such as by visual inspection (either with the unaided eye or with the assistance of a computer utilizing photographic or video protocols)

In some instances, monitoring includes visually inspecting the dissociated tissue fragments in real-time. In other instances, monitoring includes assessing the dissociated tissue fragments at regular intervals, such as every 0.01 minutes, every 0.05 minutes, every 0.1 minutes, every 0.5 minutes, every 1 minute, every 5 minutes or some other interval.

Methods of the present disclosure may also include a step of assessing the dissociated tissue fragments to identify any desired adjustments to the subject protocol. In other words, methods in these embodiments include providing feedback based evaluating the tissue fragments, where adjustments to the protocol may vary in terms of goal, where in some instances the desired adjustment are adjustments that ultimately result in an improved size homogeneity of shape homogeneity of the dissociated tissue fragments.

Where feedback provided indicates that a particular protocol is less than optimal, such as where dissociated tissue fragments have unsatisfactory size homogeneity or shape homogeneity, methods may include changing one or more parts of the subject protocols. For example, one or more parameters for pressing the biological tissue sample through the cutting blade may be adjusted. In one example, methods include adjusting the rate that the biological tissue sample is pressed through the cutting blade. In some instances, the rate is increased, such as by increasing the rate of displacing the tissue actuator by 1 mm/second or greater, such as 2 mm/second or greater, such as by 5 mm/sec or greater, such as by 10 mm/second or greater and by increasing the displacement rate of the tissue actuator by 25 mm/second or greater. In other instances, the rate is decreased, such as by decreasing the rate of displacing the tissue actuator by 1 mm/sec or greater, such as 2 mm/second or greater, such as by 5 mm/second or greater, such as by 10 mm/second or greater and by decreasing the displacement rate of the tissue actuator by 25 mm/second or greater.

In another example, the temperature within the housing of the tissue dissociator while the biological tissue sample is pressed through the cutting blade may be adjusted. For example, the temperature may be decreased, such as by 1° C. or more, such as by 2° C. or more, such as by 3° C. or more, such as by 5° C. or more, such as by 10° C. or more and including decreasing the temperature by 15° C. or more. In other embodiments, the temperature is increased by 1° C. or more, such as by 2° C. or more, such as by 3° C. or more, such as by 5° C. or more, such as by 10° C. or more and including increasing the temperature by 15° C. or more.

In certain embodiments, methods may further include washing the cutting surfaces of the cutting blade by expelling a fluid from the distal end of the tissue actuator. As described above, tissue actuators may include a fluid reservoir within the tissue actuator that is in fluid communication through holes at the distal end of the tissue actuator. Application of a positive pressure within the fluid reservoir, such as with a plunger, expels fluid through the holes. Fluid expelled from the tissue actuator may be employed to wash off biological tissue remaining on the distal end of the tissue actuator or for washing of tissue left behind on and between the cutting surfaces of the cutting blade. Depending on the amount of biological tissue remaining on or between the cutting surfaces of the cutting blade, methods may include washing the cutting blades one or more times, such as two or more times, such as three or more times, such as five or more times and including ten or more times.

In some embodiments, where a single interval is not sufficient to provide the desired dissociated tissue fragments, methods may include conducting one or more additional intervals. In these embodiments, protocols described herein for dissociating a biological tissue sample into a plurality of tissue fragments are repeated one or more times in a sequential manner. In practicing the subject methods, multiple interval protocols may include two or more intervals, such as three or more intervals, such as four or more intervals, such as five or more intervals, including ten or more intervals.

Kits

Aspects of the invention further include kits, where kits include one or more a housings, cutting blades and tissue actuators as described herein. In some instances, the kits can include one or more additional components (e.g., buffers, water, solvent etc.). In some instances, the kits may further include a biological tissue sample collection device, e.g., a lance, needle or scalpel configured to a sample of integumentary tissue, oral tissue, respiratory tissue, gastrointestinal tissue, cardiovascular tissue, endocrine tissue, genitourinary tissue, muscular tissue, nervous tissue or soft skeletal tissue, as described above.

The various components of the kits may be present in separate containers, or some or all of them may be pre-combined. For example, in some instances, one or more components of the kit, e.g., housings, cutting blades and tissue actuators, are present in a sealed pouch, e.g., a sterile foil pouch or envelope.

In addition to the above components, the subject kits may further include (in certain embodiments) instructions for assembling the subject kit components as well as for practicing the methods for dissociating a biological tissue sample as described herein. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject devices, methods, and kits find use in a variety of different applications where it is desirable to obtain biological tissue fragments having high size and shape homogeneity from a biological tissue sample. The present disclosure also finds use in applications where tissue fragments prepared from a biological sample may be desired for research, laboratory testing or for use in therapy. In some embodiments, the subject methods and devices may facilitate the obtaining a large amount of tissue fragments to be used as a research or diagnostic specimen for diseases such as cancer. Likewise, the subject methods and systems facilitate obtaining tissue fragments to be used in therapy, such as in the autologous treatment of wounds. Methods and devices of the present disclosure allow for preparing a plurality of tissue fragments from a biological tissue samples that are highly homogenous in size, shape with little waste and at a low cost.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of dissociating a biological tissue, the method comprising:
    inserting a biological tissue into a housing of a tissue dissociator, wherein the tissue dissociator comprises:
        a housing having an open distal end and a proximal end;
        a cutting blade positioned at the open distal end of the housing;
        a tissue actuator configured to be displaced along a longitudinal axis within the housing; and
    pressing the biological tissue against the cutting blades by displacing the tissue actuator from the proximal end to the distal end of the housing in a manner sufficient to produce a dissociated biological tissue comprising components of identical shape and size.

2. The method according to claim 1, further comprising dispensing a fluid from a reservoir which extends from a proximal end to a distal end within the tissue actuator.

3. The method according to claim 2, wherein the fluid is dispensed from an array of holes positioned at the distal end of the tissue actuator that are in fluid communication with the reservoir.

4. The method according to claim 3, wherein dispensing the fluid comprises displacing a plunger along a longitudinal axis from the proximal end to the open distal end within the tissue actuator to expel fluid through the holes at the distal end.

5. A kit comprising:
    a housing having an open distal end and a proximal end;
    a cutting blade positioned at the open distal end of the housing; and
    a tissue actuator configured to be displaced along a longitudinal axis within the housing.

6. A tissue dissociator comprising:
    a housing comprising an open distal end and a proximal end;
    a cutting blade positioned at the open distal end of the housing; and
    a tissue actuator configured to be displaced along a longitudinal axis within the housing.

7. The tissue dissociator according to claim 6, wherein the tissue actuator comprises tines.

8. The tissue dissociator according to claim 7, wherein the tissue actuator comprises an array of tines.

9. The tissue dissociator according to claim 6, wherein the tissue actuator comprises a fluid reservoir.

10. The tissue dissociator according to claim 9, wherein the open distal end of the tissue dissociator comprises holes in fluid communication with the fluid reservoir.

11. The tissue dissociator according to claim 10, wherein the open distal end of the tissue dissociator comprises an array of holes arranged in a grid pattern.

12. The tissue dissociator according to claim 11, wherein the open distal end of the tissue dissociator comprises an array of tines.

13. The tissue dissociator according to claim 12, wherein the holes are interspersed between the tines.

14. The tissue dissociator according to claim 9, wherein the tissue actuator further comprises a plunger configured to be displaced along a longitudinal axis within the reservoir.

15. The tissue dissociator according to claim 6, wherein the cutting blade comprises a grid configuration.

16. The tissue dissociator according to claim 15, wherein the cutting blade is configured to dissociate tissue into components of identical shape or identical size.

17. The tissue dissociator according to claim 6, further comprising an adapter positioned at the proximal end of the housing, wherein the adapter is configured to releasably connect the proximal end of the housing to an opening of the container.

18. The tissue dissociator according to claim 17, wherein the adapter comprises a latch, a notch, a pin, a groove, a tether, a hinge, a screw thread or a combination thereof.

19. The tissue dissociator according to claim 17, further comprising a container releasably attached to the proximal end of the housing.

20. The tissue dissociator according to claim 19, wherein the container is selected from the group consisting of a blood collection tube, test tube, centrifuge tube, culture tube, microtube, Eppendorf tube and syringe.

\* \* \* \* \*